United States Patent [19]

Suhonen et al.

[11] Patent Number: 5,353,820

[45] Date of Patent: Oct. 11, 1994

[54] FLAVORED DENTAL CLEANING ARTICLE AND METHOD

[75] Inventors: Christopher H. Suhonen, San Jose, Calif.; Pedro L. Jusino, Yauco, P.R.

[73] Assignee: Gillette Canada Inc., Kirkland, Canada

[21] Appl. No.: 832,151

[22] Filed: Feb. 6, 1992

[51] Int. Cl.$^5$ ............................................. A61C 15/00
[52] U.S. Cl. ...................... 132/321; 132/200
[58] Field of Search .................. 132/321, 329, 200; 8/115.54, 115.55

[56] References Cited

U.S. PATENT DOCUMENTS

| | | | |
|---|---|---|---|
| 2,667,443 | 1/1954 | Ashton | 167/93 |
| 3,516,846 | 6/1970 | Matson . | |
| 3,516,941 | 6/1970 | Matson . | |
| 3,578,545 | 5/1971 | Carson et al. . | |
| 3,755,064 | 8/1973 | Maierson . | |
| 3,771,536 | 11/1973 | Dragan | 132/89 |
| 3,778,383 | 12/1973 | Schibler et al. . | |
| 3,800,812 | 4/1974 | Jaffe | 132/89 |
| 3,830,246 | 8/1974 | Gillings | 132/89 |
| 3,837,351 | 9/1974 | Thornton | 132/89 |
| 3,896,824 | 7/1975 | Thornton | 132/89 |
| 3,897,795 | 8/1975 | Engel | 132/89 |
| 3,943,949 | 3/1976 | Ashton et al. | 132/89 |
| 4,008,727 | 2/1977 | Thornton | 132/89 |
| 4,019,522 | 4/1977 | Elbreder | 132/90 |
| 4,029,113 | 6/1977 | Guyton | 132/91 |
| 4,033,365 | 7/1977 | Klepak et al. | 132/89 |
| 4,087,376 | 5/1978 | Foris et al. . | |
| 4,089,802 | 5/1978 | Foris et al. . | |
| 4,100,103 | 7/1978 | Foris et al. . | |
| 4,142,538 | 3/1979 | Thornton | 132/89 |
| 4,162,688 | 7/1979 | Tarrson et al. | 132/92 |
| 4,251,386 | 2/1981 | Saeki et al. . | |
| 4,360,514 | 11/1982 | Buck | 424/56 |
| 4,362,712 | 12/1982 | Buck | 424/49 |
| 4,403,089 | 9/1983 | Buck | 528/247 |
| 4,414,990 | 11/1983 | Yost | 132/91 |
| 4,419,396 | 12/1983 | Sugimoto et al. . | |
| 4,528,226 | 7/1985 | Sweeny | 428/40 |
| 4,548,219 | 10/1985 | Newman et al. | 132/91 |
| 4,576,190 | 3/1986 | Youssef | 132/89 |
| 4,627,975 | 12/1986 | Lynch | 424/49 |
| 4,638,823 | 1/1987 | Newman et al. | 132/91 |
| 4,646,766 | 3/1987 | Stallard | 132/91 |
| 4,817,643 | 4/1989 | Olson | 132/329 |
| 4,911,927 | 3/1990 | Hill et al. | 424/443 |
| 4,952,392 | 8/1990 | Thame | 424/58 |

*Primary Examiner*—Gene Mancene
*Assistant Examiner*—Frank A. LaViola
*Attorney, Agent, or Firm*—Oblon, Spivak, McClelland, Maier & Neustadt

[57] ABSTRACT

A flavored interproximal dental cleaning article having an open, porous brush portion with matrix particles comprising flavor particles encapsulated in a water-soluble matrix bound to the surfaces of the brush portion by a water-insoluble, matrix particle encapsulating hard, flexible polymeric film which is preferably a urethane polymer. The brush portion can be integrally connected to a threader portion and/or a floss portion, and the threader portion and the brush portion can be further stiffened by a second outer polymeric hard flexible film coating which can be free of flavor particles. The matrix particles can be flavor oils encapsulated in a matrix comprising malto-dextrin or non-toxic gums. The cleaning article is made by impregnating a open, porous brush portion of an interproximal dental cleaning article with a coating solution comprising a coating material dissolved in a volatile solvent. The coating solution has dispersed therein matrix particles comprising flavor particles encapsulated in a water-soluble matrix, the matrix particles being substantially insoluble in the volatile solvent. The coating, preferably of a urethane polymer, is cured to substantial hardness to form an open, porous brush portion, matrix particles comprising flavor particles encapsulated in a water-soluble matrix being bound to the surfaces of the brush portion by a first water-insoluble, matrix particle encapsulating hard, flexible polymeric film.

20 Claims, 2 Drawing Sheets

FLAVORED DENTAL CLEANING ARTICLE AND METHOD

FIELD OF THE INVENTION

This invention relates to an improved favored article combining a dental brush with an optional threader and dental floss for cleaning the interproximal surfaces of teeth and to a method for manufacturing the improved article.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such a device is described in U.S. Pat. No. 4,008,727, for example, the entire contents of which are hereby incorporated by reference.

Attractive and pleasant flavors and flavor odors have been provided in dental products including dental flosses to impart a flavor to the flosses and encourage their regular use. These have been applied in the form of flavoring oils to the surface of floss or wax coating on the floss, or dispersed in wax coatings applied to the floss. U.S. Pat. No. 3,943,949 describes a plurality of filaments impregnated with a water-insoluble wax with spray-dried flavor particles being adhered to the surface of the wax coatings. U.S. Pat. No. 4,033,365 describes a plurality of filaments coated with a polymer, the coating containing spray-dried flavor particles. The coating is specified to be one of four types of polymers, one being a nylon type polymer. The spray-dried flavor particles are matrices of water-soluble materials such as gums, starches, dextrins, and the like in which the flavoring materials are dispersed. A wide variety of flavoring and wax coating materials are discloses in this patent. The entire contents of the patents listed above are hereby incorporated by reference.

SUMMARY AND OBJECTS OF THE INVENTION

The flavored interproximal dental cleaning article of this invention has an open, porous brush portion with matrix encapsulated flavoring particles further encapsulated in a water-soluble matrix bound to the surfaces of the brush portion by a binding agent. The binding agent is a first water-insoluble, matrix particle encapsulating hard, flexible polymeric film which is preferably a urethane polymer. The open, porous brush portion preferably comprises a multiple filament portion of textured yarn. The brush portion can be integrally connected to a threader portion and/or a floss portion, and the threader portion and the brush portion can be further stiffened with a second outer polymeric hard flexible film coating which can optionally be free of flavor particles. The matrix particles can be flavor oils encapsulated in a matrix comprising malto-dextrin and/or a non-toxic gum.

The process of this invention for making a flavored interproximal dental cleaning article comprises impregnating a open, porous brush portion of an interproximal dental cleaning article with a coating solution comprising a polymer coating-forming solution in a volatile solvent. The coating solution has dispersed therein matrix particles comprising flavor particles encapsulated in a water-soluble matrix, the matrix particles being substantially insoluble in the volatile solvent. The solvent is evaporated from the solution to harden the coating to substantial hardness to yield an open, porous brush portion, matrix particles comprising flavor particles encapsulated in a water-soluble matrix being bound to the surfaces of the brush portion by a first water-insoluble, matrix particle encapsulating hard, flexible polymeric film. Preferably, the process includes the additional steps of impregnating the threader portion of a preferred product with a second coating solution comprising a polymer coating-forming solution in a volatile solvent; and evaporating the solvent to harden the coating to substantial hardness to yield an interproximal dental cleaning article wherein the threader is further stiffened by a second outer polymeric hard flexible film coating.

It is an object of this invention to provide an improved interdental brush device with particulate flavors encapsulated for maximum flavor retention, the flavor particles being bound to the brush surface and encapsulated by a hard, flexible film which additionally stiffens and improves the cleaning properties of the brush portion. The flavor particles also increase the abrasivity and cleaning action of the product.

It is a further object of this invention to provide a process for manufacturing this improved interdental brush device to yield a product which retains an open, porous brush portion.

DETAILED DESCRIPTION OF THE INVENTION

Figure 1:
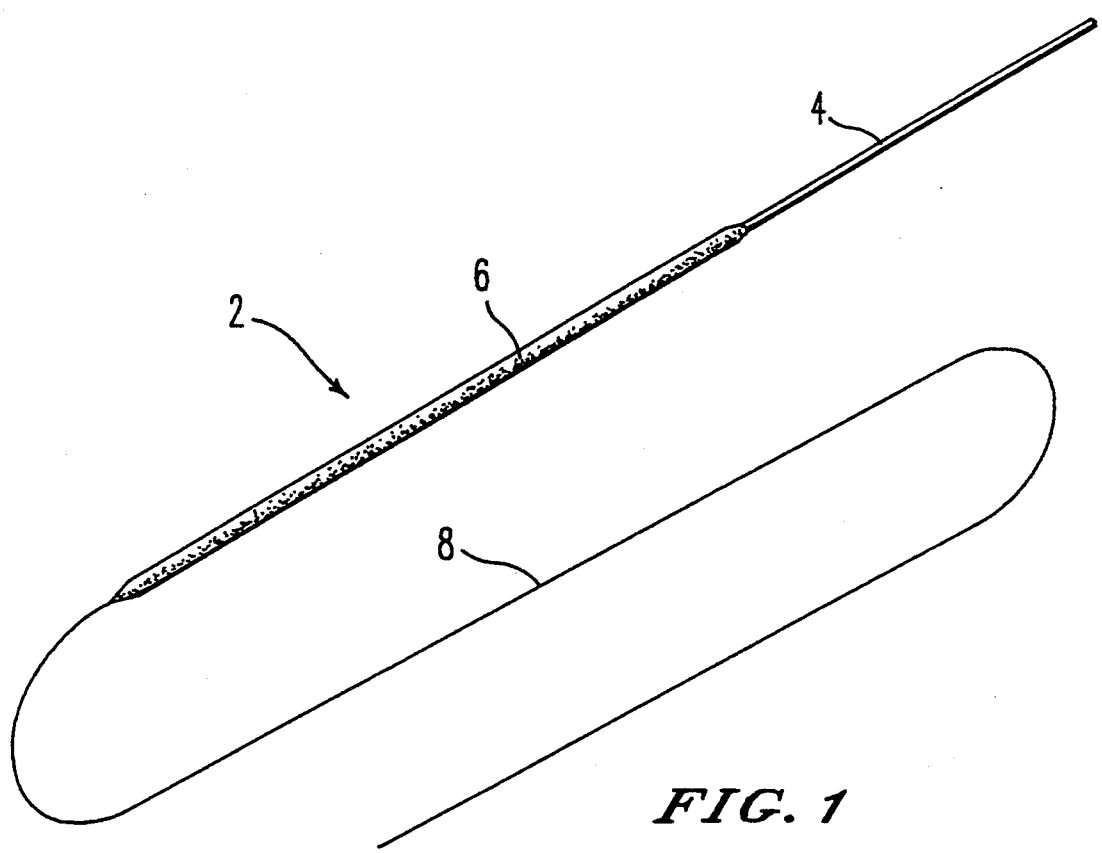
FIG. 1 is a representation of the preferred embodiment of the improved interproximal teeth cleaning article of this invention.

The elongate teeth cleaning article of this invention provides the combined functions of an interproximal brush and floss. In the representation shown in FIG. 1, the distal end of the interproximal threaded floss and brush article 2 comprises a threader portion 4 which can be inserted between two teeth to a position where it can be grasped between two fingers to draw the brush and floss portions between the teeth for cleaning. The distal end of the threader 4 is the integral proximal end of the integral brush portion 6, and the distal end of the brush portion 6 is the integral proximal end of the floss portion 8. The composition and method of manufacturing this article are described in U.S. Pat. Nos. 3,837,351 and 4,008,727. The brush portion 6 has a roughened, porous surface which provides a brush action on the tooth and gum surfaces during use. The cavities in the brush surface capture and remove food, bacterial and other materials on the tooth and gum surfaces. The brush and threader portions are stiffened by the process of this invention, improving their respective threading and cleaning action.

The embodiment of this invention in FIG. 1 is selected for detailed explanation of the invention by way of example and not by way of limitation. The FIG. 1 embodiment comprises a brush portion combined with both a threader and a floss portion and is a preferred embodiment of the invention. However, it will be readily apparent to a person skilled in the art that the cleaning article can be a brush portion without either a threader or floss portion, or it can be a brush portion combined with only a threader portion or a floss portion. All of these combinations are intended to be included in this invention.

The interproximal cleaner is manufactured from a suitable natural or synthetic textured yarn, that is, a yarn made of monofilaments which have been textured to form coils, curves, twists, crimps and loops which will stretch and return to a bulked shape.

In the initial manufacturing process, the yarn is impregnated with a binder coating polymer solution such as a nylon solution. The excess binder is removed by squeeze rollers, squeeze bars, or other removal devices. It is then dried while a portion of the stretched yarn in held under tension directly exposed to heat to form a floss string portion. Another portion of the yarn is held under tension and protected from direct exposure to heat to form the brush portion. The hardened resin coating maintains the product in this conformation during subsequent coating processes, storage and use.

Single or multiple coats of anhydrous urethane elastomers and/or anhydrous binder coating solution are then applied to threader portion 4 and brush portion 6 to increase the stiffness of the threader, thereby to facilitate its function, and to retain the resilience of the brush and its ability to maintain its bulky, open, porous characteristics during use. Some of these binder coating solutions contain encapsulated flavor particles and may contain additionally contain liquid oil-based flavors and artificial sweeteners such as cyclamates, saccharin, aspartame, xylitol and the like.

Suitable flavor particles are microglobules or spheres of flavor surrounded, encased or encapsulated with a water-soluble coating matrix such as malto-dextrin optionally containing a non-toxic gum such as gum arabic. The objective of encapsulating the flavor is to preserve the volatile, oxidizable flavor during storage and to provide a flavor burst upon disruption of the flavor coating. The additional coatings by which these particles are bound to the brush portion of the device provide an additional encapsulating layer which preserves the flavor. The binder coating is disrupted during abrasion occurring during flossing, that is, the application of the brush against the tooth surface. This disruption exposes the malto-dextrin and gum to the enzymes in the saliva, causing them to immediately disintegrate and release the flavor oils. The flavor particles also increase the abrasivity and cleaning action of the product.

These flavor particles can be made by conventional procedures such as spray-drying emulsions of flavor oils dispersed in a maltro-dexrin solution. Alternatively, they can be made by extruding, tray-drying or drum-drying the emulsions to form solids which are then ground to the desired particle size. In a still further procedure, the microencapsulated flavor particles can be made by coacervation or aqueous phase separation procedures which yield flavor droplets coated in a non-toxic coating such as gelatin. Suitable microencapsulated flavor particles and processes for manufacturing them are described by Henry B. Heath in SOURCE BOOK OF FLAVORS. Westport: The Avi Publishing Company, Inc., pp 536-532 (1981), the entire contents of this publication being hereby incorporated by reference.

Suitable spray-dried, tray or drum-dried and ground, and extruded and ground flavor particles are available from a variety of commercial sources such as MDP Industrial Food Products Division of Borden Inc. (Encapsulated Peppermint Borden #13742, Encapsulated Spearmint Borden #13587, and DURAROME® extruded flavors).

It is critical that the integrity of the matrix be maintained during the coating process. Because the matrix is water-soluble but not soluble in absolute alcohols, the coating processes require the use of coating solutions of anhydrous solvents which can contain anhydrous alcohols and in which malto-dextrins and gums are insoluble.

A most important feature of the coating materials and process is their ability to provide a thin, durable residual film which does not clog the open, porous brush structure. Application of polymers in solution to form a thin, hard and flexible coating is essential. A second purpose of the residual film is to further enhance the strength and resilience of the brush portion. The residual film envelops the encapsulated flavor, thus adhering it to the brush fibers, and creates a thin film coating on the surface of the brush fibers throughout the open, porous structure of the brush portion.

Traditional wax impregnants cannot satisfy these requirements. The soft, non-volatile waxes fill the brush, completely impregnating the structure with a soft, non-hardening, non-durable material. Waxes would fill, plug and destroy its open, porous bulky structure and eliminate its cleaning properties. The soft wax coatings would not contribute any durable stiffness to the brush portion and would eliminate its resilience.

The coating solutions should be sufficiently viscous to maintain the encapsulated flavor particles in suspension, but have a sufficient volatile solvent content to develop a thin, durable, hardened residual film coating. The most desirable thin film development and best encapsulated flavor retention is achieved through the use of anhydrous, volatile nylon and urethane coating solutions.

Additional coatings of urethane in xylene, alcohol or other suitable solvents can be applied locally to the threader portions of the brush articles having a threader portion to further stiffen the threaders, if desired, either by conventional machine or manual methods.

Figure 2:
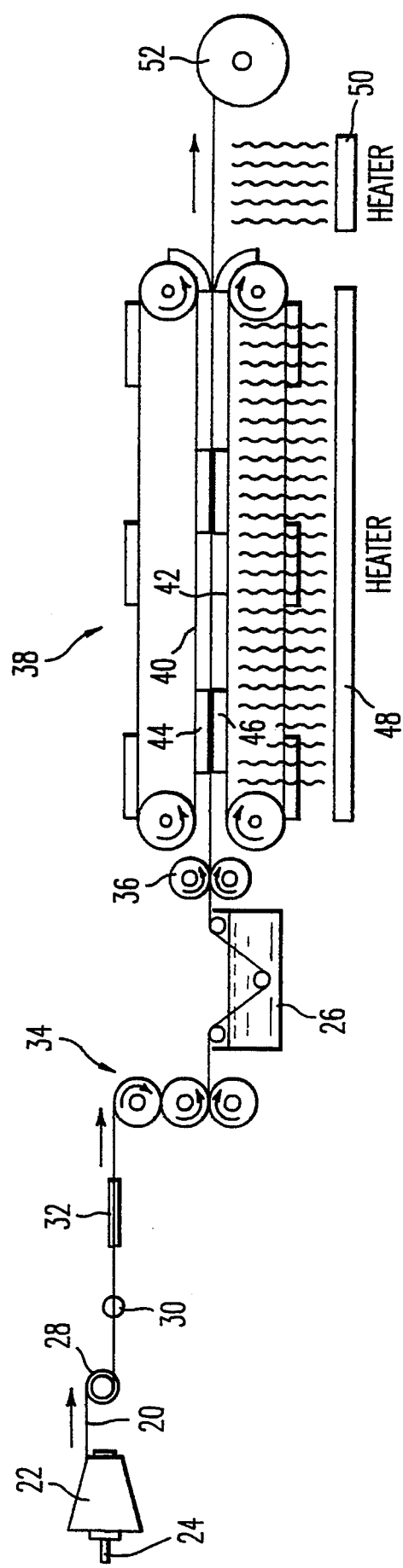
FIG. 2 is a schematic representation of a system suitable for producing the interproximal space tooth cleaning article of FIG. 1.

FIG. 2 shows a schematic representation of a system for manufacturing the flavored threaded floss and brush embodiment of this invention. The article is manufactured by processing a yarn, preferably a high tenacity nylon yarn, with nylon, polyurethane resin and flavor components in three manufacturing operations. The product is then processed through a packaging operation to provide the finished output product.

Yarn 20 is drawn from yarn package 22 (spool or cone) which is mounted on creel 24. Yarn 20 is pulled through a tensioning system which gradually applies tension before it reaches the coating bath 26. This system consists of tension disk 28, guide slot 30, pressure plates 32, and roller assembly 34. In coating bath 26, the first binder solution is applied to the yarn. The excess coating solution is removed by squeeze rollers 36. The impregnated yarn then passes into the drying chamber 38, a gear driven roller tread system. This system comprises opposed moving chains 40 and 42, the opposing faces of each moving chain having respective gripper bars 44 and 46. Heaters 48 are positioned beneath the moving chains, forcing heated air upward towards yarn 20. The portions of the yarn suspended between adjacent gripper bar pairs are exposed to the heat, and the exposed coating is completely dried and hardened (the solvent is substantially vaporized) by the time it reaches the exit of the drying chamber 38. The exposed, dried portions retain the thin configuration formed under tension, producing the threader and floss portion. The portions of the yarn held between the gripper bars are protected from the heat and experience less solvent loss during the period of high tension. Consequently, when the yarn tension is relaxed after emerging from the heater section 38, these undried portions return to a bulk configuration to produce the brush portion. The yarn then passes over heater 50 where the residual solvent in the brush portion is evaporated, stiffening the brush portion in its bulky configuration. The yarn is then rolled in hanks under slight tension onto reel 52.

Figure 3:
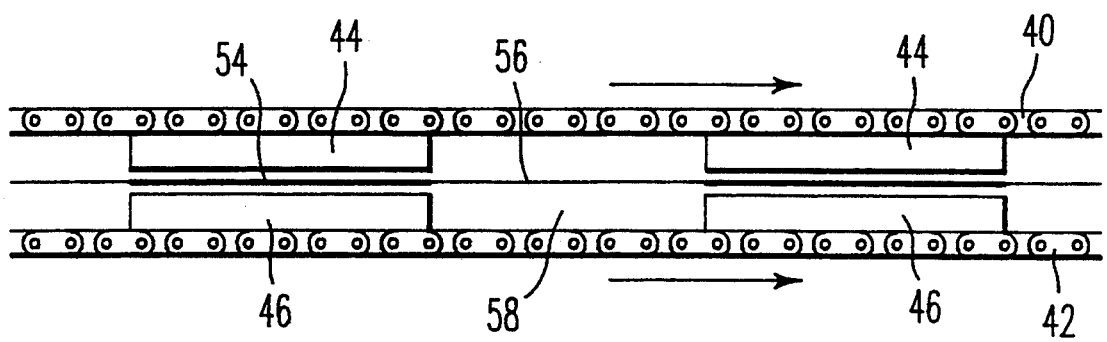
FIG. 3 is a detailed schematic representation of a portion of the drier and heater assembly shown in FIG. 2.

In the detailed schematic representation of a portion of the drier and heater assembly in FIG. 3, one portion of the yarn 54 corresponding to the brush is held between opposed moving pads or bars 44 and 46, and a second portion of the yarn 56 corresponding to the floss and threader portion is exposed to heat in the open space 58 while under tension. The solvent is rapidly evaporated from the threader and floss portion as it is transported through the heater and drier, permanently setting these portions in the thin, thread configuration formed under tension. The solvent on the brush portion is shielded from the direct heat by bars 44 and 46, producing a lower evaporation rate. When released, the shielded yarn has not completely dried. As it is relaxed, the previously shielded yarn contracts and becomes "puffy", forming the open, porous brush configuration. The drying is completed by exposing the brush to heated air.

The subsequent coatings can be applied by conventional manual processes to the final product shown in FIG. 1, cut to final lengths and taped in bundles of 50 or more individual strands. A final coating is optionally applied to the threader and/or brush portion to thicken them.

Alternatively, the subsequent coatings can be applied by conventional continuous processes to the continuous product having alternating threader/floss and brush portions. The product with the first coating completely dried is treated with a second coating bath containing microencapsulated flavoring particles. If applied to the continuous product, it can be rolled onto spools for storage or immediately cut into sections shown in FIG. 1. A final coating is optionally applied to the threader and/or brush portion to thicken it.

The dental floss yarn can be formed from a plurality of filaments of suitable substrate materials such as those described in U.S. Pat. No. 3,943,949, for example. Suitable filaments include high and normal tenacity nylon such as nylon 6 and nylon 66, DACRON, acetate polymers, and the like as well as cotton, wool and other staple fibers which can be formed into a yarn. The number of fibers are selected to yield a thread, under tension, which can be inserted in the interproximal areas between the teeth.

The first binder coating can be any polymer which is acceptable in an oral dental product and which effectively binds the fibers into an integral thread. Examples of suitable coatings are described in U.S. Pat. No. 4,033,365, for example, the entire contents of which are hereby incorporated by reference. The preferred binders are nylon polymers, applied in an anhydrous ethanol solution.

The second binder coating contains the microencapsulated flavor particles in a suitable binder solution which does not destroy the integrity of the particles. These particles comprise flavor oils dispersed or encapsulated in a suitable matrix or coating which dissolves in water and/or is metabolized by saliva enzymes. Suitable binders include non-toxic gums such as gum acacia, gum arabic, gum tragacanth and the like, starches and starch metabolites such as corn starch and dextrins, and the like. Suitable flavors include peppermint, spearmint, wintergreen, cassia, cinnamon, and the like; and fruit flavors such as cherry, strawberry, lime and the like. Suitable encapsulated flavor particles are described in U.S. Pat. Nos. 3,943,949, 3,957,964, 4,033,365, 4,071,614, 4,386,106, 4,515,769, 4,568,560 and 5,004,595, for example. The encapsulated flavors can be prepared by dispersing the flavors in the matrix solution. The matrix solution is then solidified, for example by drum drying, extrusion or spray-drying. The solid matrix formed by drum drying or extrusion are ground to provide particles having the desired size. The spray-drying process produces particles directly.

The second binder can be any suitable non-toxic substance which will retain the particles in the brush portion of the threaded brush floss article of this invention. Waxes or non-wax polymers disclosed in U.S. Pat. No. 4,033,365 can not be used because they destroy the uniquely advantageous cleaning properties of the open, porous brush. However, polyurethanes which are soluble in aromatic hydrocarbons such as xylene containing only sufficient alcohol to solubilize sweeteners are preferred, since these solvents do not significantly disturb hardened nylon primary coatings and do not dissolve matrix materials such as dextrins, for example.

One or more final coatings of urethane solution in xylene or alcohol can be applied locally to the threader portions of the threaded floss brush articles to further stiffen the threaders, if desired, either by conventional machine or by hand methods.

Additional non-toxic coatings such as silicone oil lubricants (for example, dimethylpolysiloxane oil, Dow Corning 200 Fluid, 350 cSt), dyes or other substances which will not plug the pores of the brush portion can also be applied to the final product. These liquids can be applied with conventional kiss rollers, immersed in a vat of the respective liquid, followed by a squeeze roller to remove excess liquid from the yarn.

An optimum base coating solution comprises 75% (v/v) nylon polymer (GENTAL 101, General Plastics Corporation) and 25% (v/v) anhydrous ethanol.

An optimum secondary flavor coating composition has the following composition:

| Component | Amount |
|---|---|
| Urethane Prepolymer[a] | 1000 mL |
| NOVILLE FLAVOR #62082[b] | 500 mL |
| Saccharin[c] | 14 g |
| Xylene | 450 mL |
| Encapsulated Peppermint #MCP 20190[d] | 68.7 g |
| Encapsulated Spearmint #MCP 20189[d] | 31.2 g |

[a]SPENKEL M21-40X, Spencer-Kellog Products
[b]Noville Essential Oil Company
[c]Alternatively, another sweetener such as aspartame or xylitol can be substituted in amounts yielding the desired sweetening.
[d]Borden, Inc., encapsulated, drum-dried, ground flavor particles. Alternative encapsulated, extruded, ground DURAROME ® flavor particles can also be used.

An alternative secondary flavoring coating has the following composition:

| Urethane Prepolymer[e] | 2000 mL |
|---|---|
| NOVILLE FLAVOR #62082[f] | 1900 mL |
| Saccharin[g] | 29 g |
| Absolute ethanol[g] | 100 mL |
| Encapsulated Peppermint #13499[h] | 275 g |
| Encapsulated Spearmint #13587[h] | 125 g |

[e]SPENKEL M21-40X, Spencer-Kellog Products
[f]Noville Essential Oil Company
[g]Alternatively, another sweetener such as aspartame or xylitol can be substituted in amounts yielding the desired sweetening.
[h]Borden, Inc. Alternative DURAROME ® flavor particles can also be used.

An optimum secondary plain coating composition can comprise 1500 mL of urethane prepolymer in 1500 mL of anhydrous methyl ethyl ketone solvent.

We claim:

1. A flavored interproximal dental cleaning article having an open, porous brush portion, matrix particles comprising flavor particles encapsulated in a water-soluble matrix being bound to the surfaces of the brush portion by a first water-insoluble, matrix particle encapsulating hard, flexible polymeric film formed from a coating solution in which the water-insoluble matrix is substantially insoluble.

2. A flavored interproximal dental cleaning article of claim 1 wherein the first polymeric film comprises a urethane polymer.

3. A flavored interproximal dental cleaning article of claim 1 wherein the open, porous brush portion comprises a multiple filament portion of textured yarn.

4. A flavored interproximal dental cleaning article of claim 1 including a threader portion which is integral with the brush portion.

5. A flavored interproximal dental cleaning article of claim 4 wherein the threader portion is stiffened by a second outer polymeric hard flexible film coating which is free of flavor particles.

6. A flavored interproximal dental cleaning article of claim 5 wherein the second outer flexible polymeric film coating comprises a urethane polymer.

7. A flavored interproximal dental cleaning article of claim 1 wherein a floss portion is integral with the brush portion.

8. A flavored interproximal dental cleaning article of claim 1 wherein a threader portion and a floss portion are integral with the brush portion.

9. A flavored interproximal dental cleaning article of claim 1 wherein the matrix particles are flavor oils encapsulated in a matrix comprising malto-dextrin.

10. A flavored interproximal dental cleaning article of claim 9 wherein the matrix particles have been prepared by a process comprising drum-drying a matrix solution containing flavoring oils.

11. A flavored interproximal dental cleaning article of claim 9 wherein the matrix particles have been prepared by a process comprising extruding a matrix solution containing flavoring oils.

12. A flavored interproximal dental cleaning article of claim 9 wherein the matrix particles have been prepared by a process comprising spray-drying a matrix solution containing flavoring oils.

13. A process for making a flavored interproximal dental cleaning article comprising
  a) coating an open, porous brush portion of an interproximal dental cleaning article with a solution comprising a polymer coating-forming compound in a volatile solvent, the coating solution having dispersed therein matrix particles comprising flavor particles encapsulated in a water-soluble matrix, the matrix particles being substantially insoluble in the volatile solvent; and
  b) evaporating the solvent to harden the coating to substantial hardness to form an open, porous brush portion, matrix particles comprising flavor particles encapsulated in a water-soluble matrix being bound to the surfaces of the brush portion by a first water-insoluble, matrix particle encapsulating hard, flexible polymeric film.

14. A process of claim 13 wherein the particles have been prepared by a process comprising drum-drying a matrix solution containing flavoring oils.

15. A process of claim 13 wherein the particles have been prepared by a process comprising extruding a matrix solution containing flavoring oils.

16. A process of claim 13 wherein the particles have been prepared by a process comprising spray-drying a matrix solution containing flavoring oils.

17. A process of claim 13 for making a flavored interproximal dental cleaning article having an integral threader portion including the additional steps of
  c) coating the threader portion of the product of step (b) with a second coating solution comprising a polymer coating-forming compound in a volatile solvent; and
  d) evaporating the solvent to harden the coating to substantial hardness to form an interproximal dental cleaning article wherein the brush portion is stiffened by a second outer polymeric hard flexible film coating.

18. A process of claim 17 wherein the second coating solution and the second outer coating do not contain flavoring particles.

19. A process of claim 17 wherein at least one polymer-forming compound is a urethane compound.

20. A process of claim 19 wherein at least one polymer-forming compound is a soluble urethane prepolymer.

* * * * *